US 11,517,667 B2

(12) United States Patent
Osawa et al.

(10) Patent No.: US 11,517,667 B2
(45) Date of Patent: Dec. 6, 2022

(54) PUNCTURE NEEDLE (71) Applicant: TERUMO KABUSHIKI KAISHA, Tokyo (JP)

(72) Inventors: Kosuke Osawa, Ebina (JP); Takehiko Ueda, Kofu (JP); Masahiko Nagasawa, Kai (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 14 days.

(21) Appl. No.: 17/204,097

(22) Filed: Mar. 17, 2021

(65) Prior Publication Data
US 2021/0196886 A1 Jul. 1, 2021

Related U.S. Application Data (63) Continuation of application No. PCT/JP2019/033066, filed on Aug. 23, 2019.

(30) Foreign Application Priority Data

Sep. 27, 2018 (JP) .............................. JP2018-182413

(51) Int. Cl.
*A61M 5/158* (2006.01)
*A61M 5/42* (2006.01)
(Continued)

(52) U.S. Cl.
CPC ............ *A61M 5/158* (2013.01); *A61M 5/427* (2013.01); *A61B 8/0841* (2013.01);
(Continued)

(58) Field of Classification Search
CPC ................. A61M 5/158; A61M 5/427; A61M 2205/3375; A61M 5/32;
(Continued)

(56) References Cited

U.S. PATENT DOCUMENTS 5,201,715 A * 4/1993 Masters ................ A61M 5/427
600/459
5,759,154 A 6/1998 Hoyns
(Continued)

FOREIGN PATENT DOCUMENTS

JP 3171525 B2 5/2001
JP 2015-213627 12/2015
WO WO-2007/013130 A1 2/2007

OTHER PUBLICATIONS

International Searching Authority, "Written Opinion," issued in connection with International Patent Application No. PCT/JP2019/033066, dated Nov. 12, 2019.
(Continued)

*Primary Examiner* — Bhisma Mehta
*Assistant Examiner* — Phoebe Anne Staton
(74) *Attorney, Agent, or Firm* — Foley & Lardner LLP (57) ABSTRACT A hollow puncture needle includes: a needle body portion; a needle distal end portion that extends from the needle body portion in a distal direction and that includes a blade surface that is inclined with respect to an axis of the puncture needle; and an ultrasonic wave reflecting structure including at least one reflecting portion having a concave or hole shape that opens on an inner peripheral surface of the needle distal end portion. An inner surface of the reflecting portion includes a pair of inclined surfaces that face each other, wherein a distance between the inclined surfaces becomes smaller in a direction towards an outer peripheral surface side of the needle distal end portion. The inclined surfaces is parallel to the axis of the puncture needle.

23 Claims, 11 Drawing Sheets (51) Int. Cl.
 *A61B 8/08* (2006.01)
 *A61B 90/00* (2016.01)
(52) U.S. Cl.
 CPC ............... *A61B 2090/3925* (2016.02); *A61M 2005/1588* (2013.01); *A61M 2205/3375* (2013.01)
(58) Field of Classification Search
 CPC ... A61M 2005/1588; A61B 2017/3413; A61B 8/0841; A61B 2090/3925; A61B 17/3403; A61B 17/3421
 See application file for complete search history.

(56) References Cited

U.S. PATENT DOCUMENTS

| | | | | |
|---|---|---|---|---|
| 2002/0151797 | A1* | 10/2002 | Montegrande | A61B 90/39 600/458 |
| 2012/0116248 | A1* | 5/2012 | McWeeney | A61B 10/0233 600/567 |
| 2014/0276073 | A1* | 9/2014 | Quearry | A61B 17/3421 600/458 |
| 2017/0224376 | A1* | 8/2017 | Kuracina | A61B 8/0841 |

OTHER PUBLICATIONS

International Searching Authority, "International Search Report," issued in connection with International Patent Application No. PCT/JP2019/033066, dated Nov. 12, 2019.

* cited by examiner

PUNCTURE NEEDLE

CROSS-REFERENCE TO RELATED APPLICATIONS

This application is a bypass continuation of PCT Application No. PCT/JP2019/033066, filed on Aug. 23, 2019, which claims priority to Japanese Application No. 2018-182413, filed on Sep. 27, 2018. The contents of these applications are hereby incorporated by reference in their entireties.

BACKGROUND

The present disclosure relates to a puncture needle capable of puncturing a position of the puncture needle is detected by using reflection of ultrasonic waves.

For example, an indwelling needle including a catheter (outer needle) and a puncture needle (inner needle) is used to infuse a nutrient to a patient. When puncturing is performed with such an indwelling needle, for example, an operation is performed while ultrasonic waves are emitted from an ultrasonic imaging device for confirmation of a position of a blood vessel to be punctured. The puncture needle performing the puncturing is also irradiated with the ultrasonic waves for confirmation of a position of the puncture needle with an image obtained on the basis of reflected waves of the ultrasonic waves. As such an indwelling needle, one is conventionally known that is provided with a groove for ultrasonic wave reflection on the outer peripheral surface of the puncture needle (see, for example, JP 3171525 B2).

SUMMARY

In the conventional puncture needle including the groove for ultrasonic wave reflection, the groove is provided on the outer peripheral surface of the puncture needle (the outer peripheral surface on the proximal end side from the blade surface), so that it is difficult to accurately recognize a position of a needle distal end portion including the blade surface. Furthermore, depending on an angle around an axis of the puncture needle with respect to a puncture site, the ultrasonic waves may not be reflected toward a probe of the ultrasonic imaging device, in which case a desired echo image cannot be obtained.

Thus, an object of certain embodiments of the present invention is to provide a puncture needle in which the position of the needle distal end portion can be easily recognized, where the puncture needle can reflect the ultrasonic waves toward the probe of the ultrasonic imaging device even when the angle around the axis of the puncture needle with respect to the puncture site changes.

One embodiment is directed to a hollow puncture needle that includes an ultrasonic wave reflecting structure. The puncture needle includes: a needle body portion; and a needle distal end portion extending from the needle body portion in a distal direction and including a blade surface inclined with respect to an axis of the puncture needle. The ultrasonic wave reflecting structure includes at least one reflecting portion having a concave or hole shape that opens on an inner peripheral surface of the needle distal end portion. An inner surface of the reflecting portion includes a pair of inclined surfaces facing each other and having a distance from each other that becomes smaller as it is closer to an outer peripheral surface side of the needle distal end portion. Each of the pair of the inclined surfaces is parallel to the axis of the puncture needle.

According to the puncture needle of the present invention, because the ultrasonic wave reflecting structure is provided on the inner peripheral surface of the needle distal end portion, the position of the needle distal end portion can be easily recognized from the obtained echo image. Furthermore, even if the angle around the axis of the puncture needle with respect to the puncture site changes, the ultrasonic waves can be reflected toward the probe of the ultrasonic imaging device by the reflecting portion including a pair of reflecting surfaces. It is therefore possible to efficiently reflect the ultrasonic waves and obtain a clearer echo image.

DETAILED DESCRIPTION

Hereinafter, a plurality of suitable embodiments of the puncture needle according to the present invention will be described with reference to the accompanying drawings. Note that, in a second embodiment, the same or similar elements as those in a first embodiment are designated by the same reference numerals, and detailed description thereof will be omitted.

Figure 1:
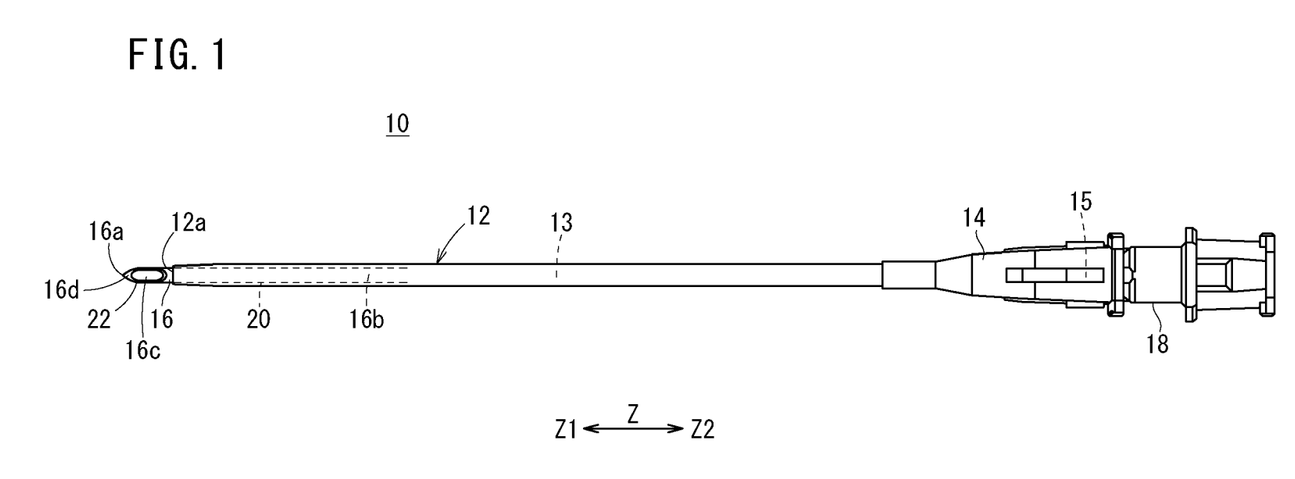
FIG. 1 is a plan view of an indwelling needle including a puncture needle according to a first embodiment of the present invention.

An indwelling needle 10 illustrated in FIG. 1 includes a catheter 12, a catheter hub 14 coupled to a base end portion (an end portion in an arrow Z2 direction side) of the catheter 12, a puncture needle 16 removably inserted into the catheter 12, and a needle hub 18 coupled to a base end portion of the puncture needle 16. The indwelling needle 10 is, in other words, a catheter assembly.

The indwelling needle 10 forms a multi-tube structure (multi-tube portion) in which the catheter 12 and the puncture needle 16 are overlapped in an initial state before use. The indwelling needle 10 is configured as, for example, a venous catheter such as a peripheral venous catheter, or an arterial catheter such as a peripheral arterial catheter. The indwelling needle 10 may be configured as a catheter longer than the peripheral venous catheter (for example, a central venous catheter, a PICC, a midline catheter, and the like).

The catheter 12 is, for example, a hollow member including a transparent resin material and having flexibility. In the catheter 12, a cavity 13 is formed capable of accommodating the puncture needle 16 and allowing a drug solution, blood, or the like to flow.

The catheter hub 14 is, for example, a hollow member including a hard resin material. Inside the catheter hub 14, a hollow portion 15 is provided that communicates with the cavity 13 of the catheter 12 and allows an infusion solution to flow. The catheter hub 14 is exposed on a patient's skin with the catheter 12 inserted into a blood vessel, is attached with tape or the like, and is placed together with the catheter 12.

The puncture needle 16 is configured as a hollow tube having rigidity capable of puncturing a skin of a living body, and is arranged to penetrate through the cavity 13 of the catheter 12 and the hollow portion 15 of the catheter hub 14. The puncture needle 16 is formed to have a total length longer than that of the catheter 12, and is provided with a sharp needle tip 16a at the tip. A lumen 16b having a circular cross section is provided inside the puncture needle 16. The lumen 16b penetrates in an axial direction (arrow Z direction. hereinafter, referred to as "needle axis direction") of the puncture needle 16, and communicates with a distal opening 16c of the puncture needle 16.

The puncture needle 16 includes a needle body portion 20 and a needle distal end portion 22 extending from the needle body portion 20 in a distal direction (arrow Z1 direction). The needle body portion 20 is a tubular body that constitutes a main portion (portion other than the needle distal end portion 22) of the puncture needle 16. Examples of the constituent material of the puncture needle 16 include: metal material such as stainless steel, aluminum or aluminum alloy, or titanium or titanium alloy; hard resin; ceramics; and the like.

In the initial state of the indwelling needle 10 illustrated in FIG. 1, the needle distal end portion 22 is positioned on the distal side from a distal side opening 12a of the catheter 12.

Figure 2:
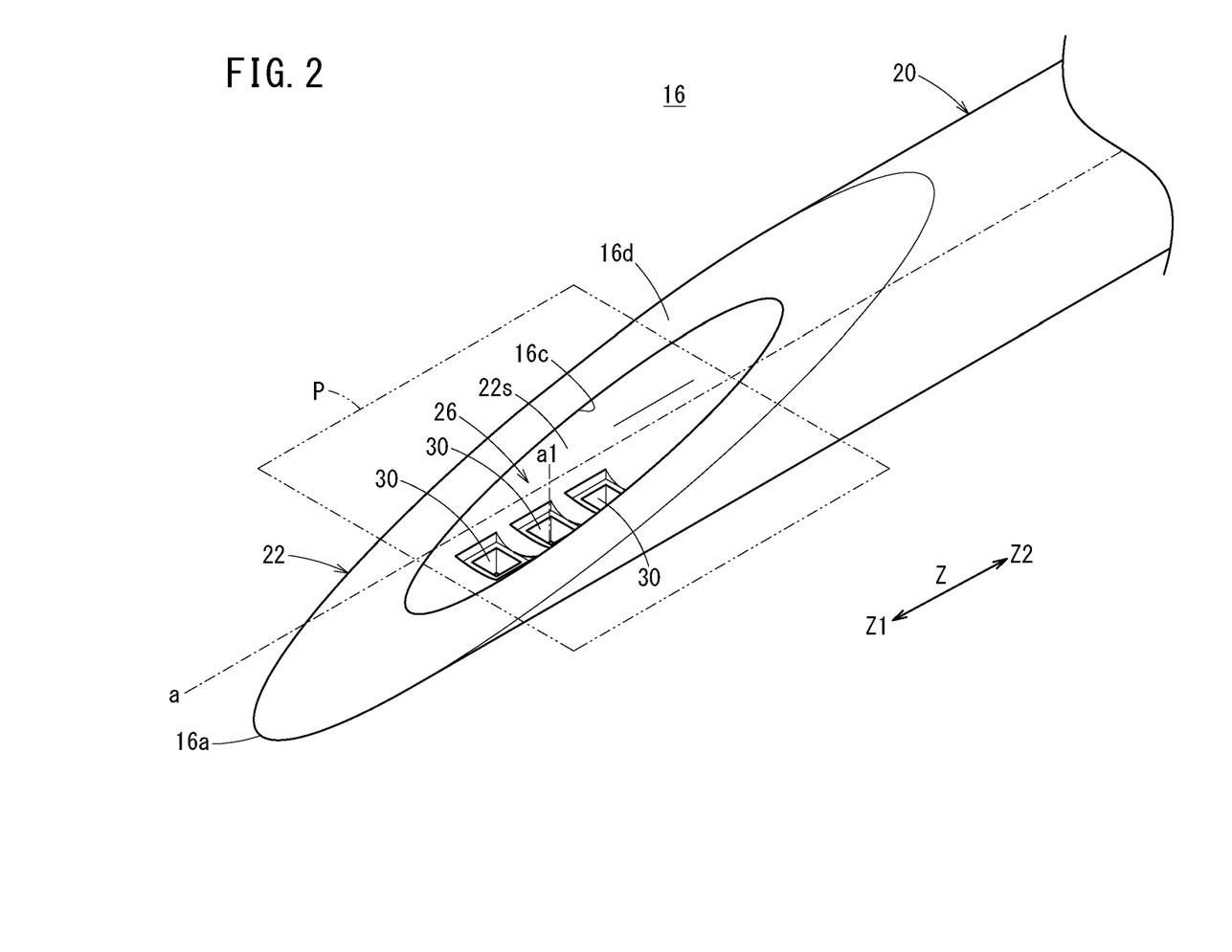
FIG. 2 is a perspective view of a distal portion of the puncture needle according to the first embodiment.
Figure 3:
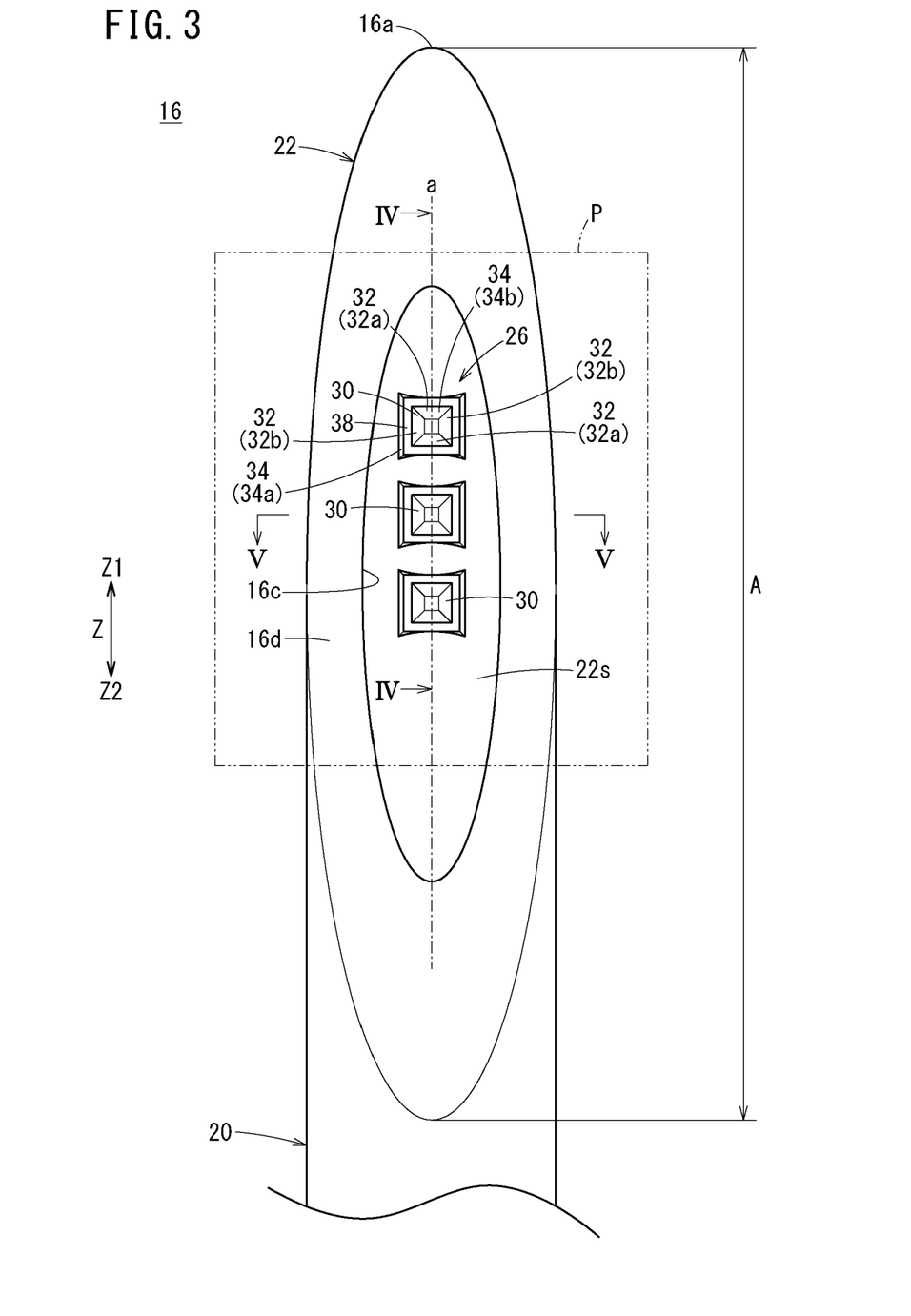
FIG. 3 is a plan view of the distal portion of the puncture needle according to the first embodiment.

As illustrated in FIGS. 2 and 3, a blade surface 16d is included that is inclined with respect to an axis a (hereinafter, also referred to as "needle axis a") of the puncture needle 16. The blade surface 16d surrounds the distal opening 16c over the entire periphery. The needle distal end portion 22 is a portion from the needle tip 16a to the base end of the blade surface 16d (a portion in a range indicated by an arrow A in FIG. 3) of the puncture needle 16.

The needle distal end portion 22 is provided with an ultrasonic wave reflecting structure 26 that reflects ultrasonic waves. Specifically, the ultrasonic wave reflecting structure 26 includes at least one reflecting portion 30 having a concave or hole shape that opens on an inner peripheral surface 22s having an arc shape of the needle distal end portion 22. These reflecting portions 30 include openings independent (distinguishable) from each other at least in the inner peripheral surface 22s of the needle distal end portion 22.

In the present embodiment, the ultrasonic wave reflecting structure 26 includes a plurality of the reflecting portions 30. The plurality of reflecting portions 30 is arranged in a straight line with a distance from each other along the needle axis a. As illustrated in FIG. 3, the plurality of reflecting portions 30 is arranged at positions overlapping the needle axis a in a plan view facing the blade surface 16d. In another aspect, the plurality of reflecting portions 30 may be arranged adjacent to each other without any distance from each other. In another aspect, the ultrasonic wave reflecting structure 26 may include only one reflecting portion 30.

A contour shape of the reflecting portion 30 when viewed along the depth direction of the reflecting portion 30 is a quadrangular shape. The reflecting portion 30 is formed in a truncated quadrangular pyramid shape. In another aspect, the reflecting portion 30 may be formed in a quadrangular pyramid shape. The reflecting portion 30 may be formed in a hole shape penetrating from the inner peripheral surface 22s of the needle distal end portion 22 to the outer peripheral surface.

Here, as illustrated in FIG. 2 and the like, a virtual surface P is defined that is perpendicular to an axis a1 in the depth direction of the reflecting portion 30. As illustrated in FIG. 3, the inner surface of the reflecting portion 30 includes four inclined surfaces 32 each inclined with respect to the virtual surface P. Inclination angles of the four inclined surfaces 32 with respect to the virtual surface P are the same as each other. In another aspect, the inclination angles of the four inclined surfaces 32 do not have to be the same as each other.

Figure 4:
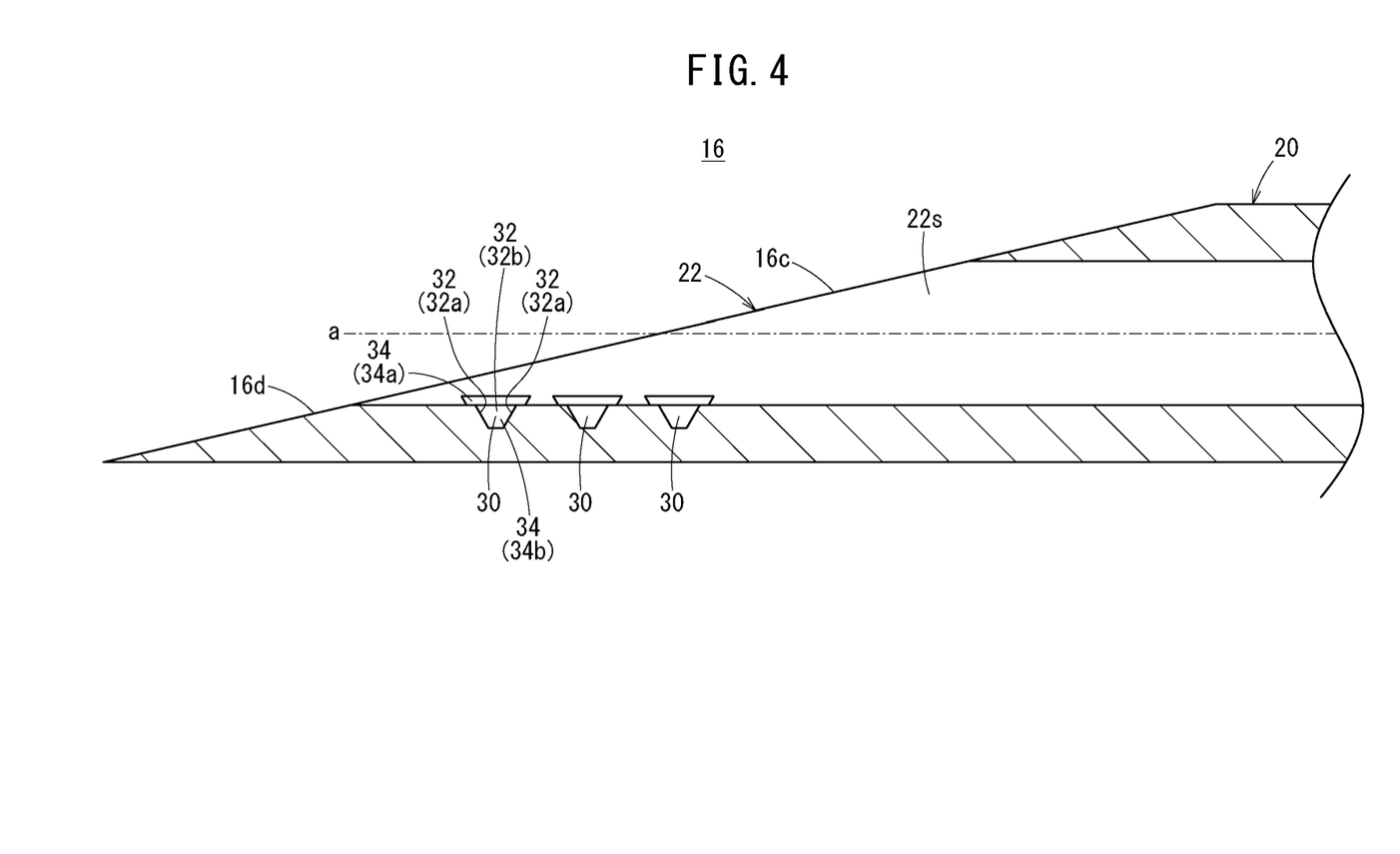
FIG. 4 is a cross-sectional view of the puncture needle taken along a line IV-IV of FIG. 3.
Figure 5:
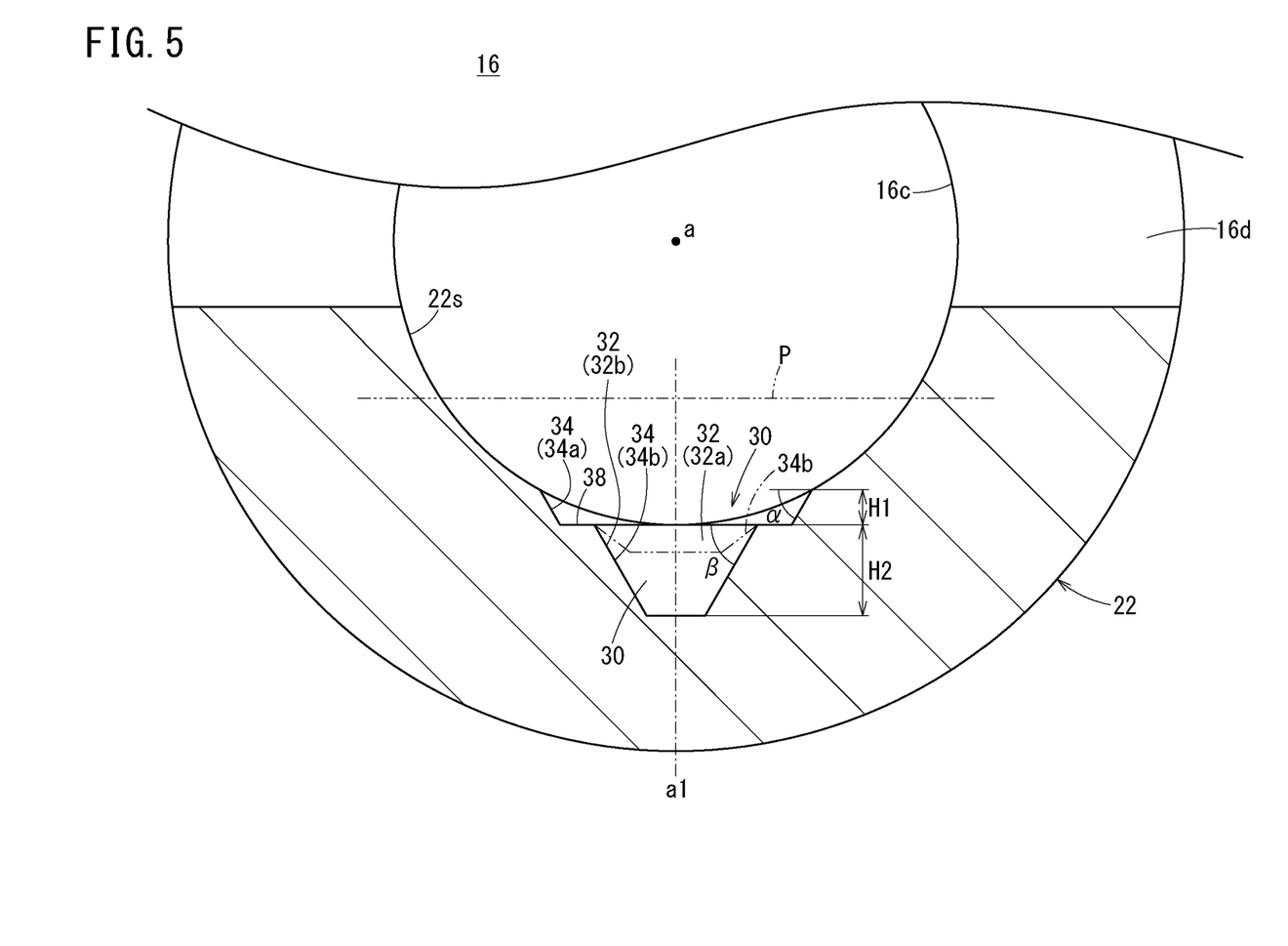
FIG. 5 is a cross-sectional view of the puncture needle taken along a line V-V of FIG. 3.

Specifically, the inner surface of the reflecting portion 30 includes a pair of inclined surfaces 32a and 32a facing each other in the needle axis direction (arrow Z direction), and another pair of inclined surfaces 32b and 32b facing each other and each parallel to the needle axis a. As illustrated in FIG. 4, the pair of inclined surfaces 32a and 32a have a distance from each other that becomes smaller as it is closer to the outer peripheral surface side of the needle distal end portion 22. As illustrated in FIG. 5, the pair of inclined surfaces 32b and 32b have a distance from each other that becomes smaller as it is closer to the outer peripheral surface side of the needle distal end portion 22.

As illustrated in FIGS. 3 and 5, each of the pair of inclined surfaces 32b and 32b includes a plurality of inclined flat surfaces 34 having depths from the inner peripheral surface 22s different from each other. In the present embodiment, the plurality of inclined flat surfaces 34 includes a first inclined flat surface 34a, and a second inclined flat surface 34b formed at a deeper position from the inner peripheral surface 22s than that of the first inclined flat surface 34a. In FIG. 5, a height H2 of the second inclined flat surface 34b along the axis a1 of the reflecting portion 30 is greater than a height H1 of the first inclined flat surface 34a along the axis a1 of the reflecting portion 30. In another aspect, the height H2 of the second inclined flat surface 34b may be the same as the height H1 of the first inclined flat surface 34a or less than the height H1 of the first inclined flat surface 34a.

An inclination angle α of the first inclined flat surface 34a with respect to the virtual surface P is set, for example, in a range of 15° to 75°, preferably in a range of 30° to 60°. In FIG. 5, the inclination angle α of the first inclined flat surface 34a with respect to the virtual surface P is set to 60°. An inclination angle β of the second inclined flat surface 34b with respect to the virtual surface P is set, for example, in a range of 15° to 75°, preferably in a range of 30° to 60°. In FIG. 5, the inclination angle β of the second inclined flat surface 34b with respect to the virtual surface P is set to 60°.

The first inclined flat surface 34a and the second inclined flat surface 34b have the same inclination angle with respect to the virtual surface P as each other. In another aspect, the plurality of inclined flat surfaces 34 may have inclination angles with respect to the virtual surface P different from each other. For example, as illustrated by a virtual line in FIG. 5, the second inclined flat surface 34b may have a smaller inclination angle with respect to the virtual surface P than that of the first inclined flat surface 34a. In another aspect, only one of the pair of inclined surfaces 32b and 32b may include the plurality of inclined flat surfaces 34.

As illustrated in FIGS. 3 and 5, an intermediate flat surface 38 parallel to the virtual surface P is provided between the plurality of inclined flat surfaces 34 (the first inclined flat surface 34a and the second inclined flat surface 34b). In the first embodiment in which the reflecting portion 30 is formed in the truncated quadrangular pyramid shape, the intermediate flat surface 38 is formed in a quadrangular ring shape. In another aspect, the intermediate flat surface 38 does not have to be provided. The reflecting portions 30 each only need to include at least the pair of inclined surfaces 32b and 32b parallel to the needle axis a, and in another aspect, the contour shape of the reflecting portion 30 when viewed along the depth direction of the reflecting portion 30 may be a shape other than the quadrangular shape, for example, a hexagonal shape or the like.

Next, a function will be described of the indwelling needle 10 including the puncture needle 16 configured as described above.

Figure 6:
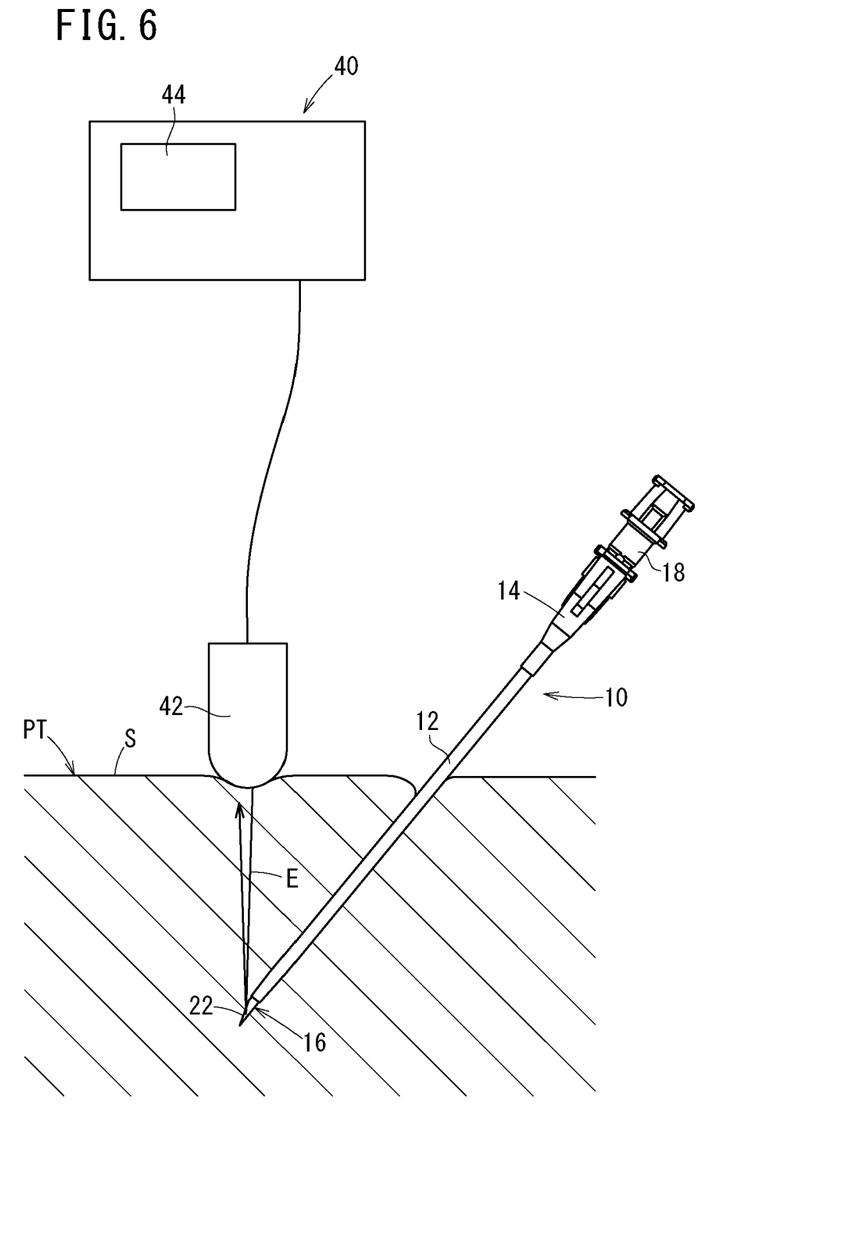
FIG. 6 is a diagram illustrating a use state of the indwelling needle.

As illustrated in FIG. 6, in use of the indwelling needle 10, puncturing of the indwelling needle 10 is performed from a skin S (puncture site) of a patient PT toward a blood vessel. At that time, a probe 42 of an ultrasonic imaging device 40 is pressed against a vicinity of the puncture site of the patient PT, and ultrasonic waves (echo beam) E are emitted. The probe 42 is configured to be able to emit the ultrasonic waves E and receive reflected waves (reflected echoes) of the ultrasonic waves E. The ultrasonic waves E are emitted from the skin S surface of the patient PT toward the inside, and irradiate a distal portion of the indwelling needle 10. Then, the ultrasonic waves E are reflected to the probe 42 side by the ultrasonic wave reflecting structure 26 (see FIG. 2) provided on the needle distal end portion 22. The ultrasonic imaging device 40 generates an echo image on the basis of the reflected waves received by the probe 42, and displays the generated echo image on a display 44.

In this case, the puncture needle 16 according to the present embodiment has the following effects.

Figure 7A:
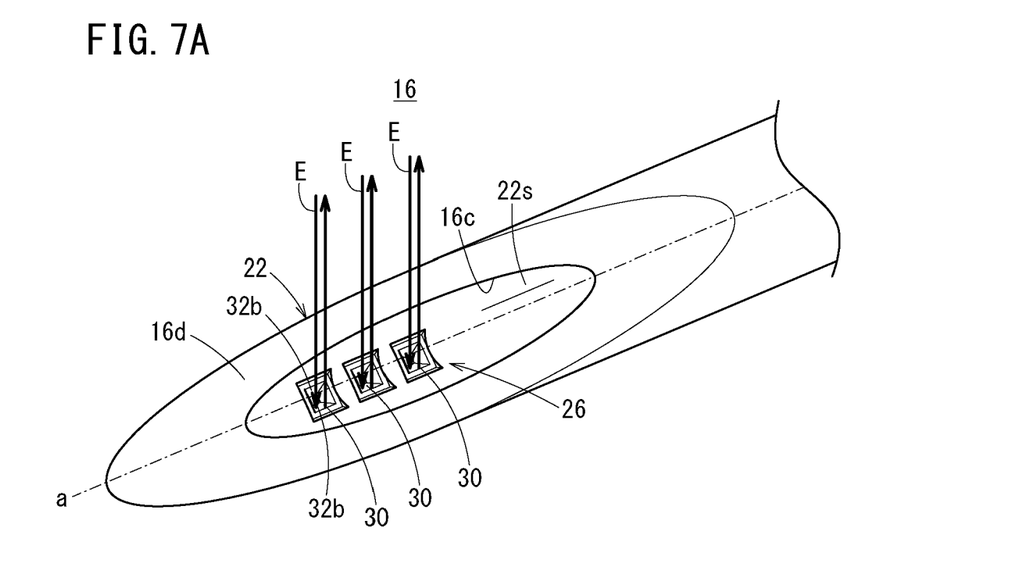
FIG. 7A is a first diagram illustrating a function of the ultrasonic wave reflecting structure of the puncture needle according to the first embodiment.
Figure 7B:
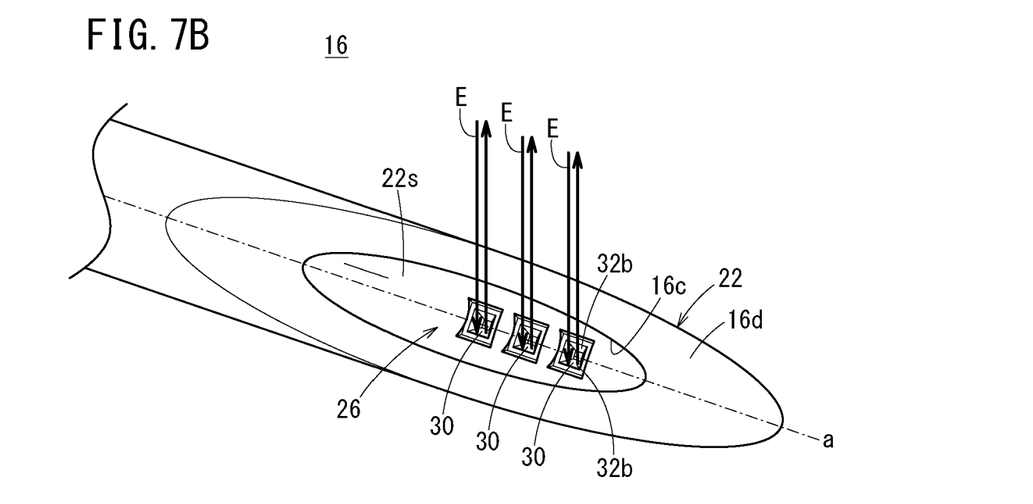
FIG. 7B is a second diagram illustrating the function of the ultrasonic wave reflecting structure of the puncture needle according to the first embodiment.

According to the puncture needle 16, as illustrated in FIG. 2 and the like, because the ultrasonic wave reflecting structure 26 is provided on the inner peripheral surface 22s of the needle distal end portion 22, a position of the needle distal end portion 22 (a distal end portion of the puncture needle 16) can be easily recognized from the obtained echo image. Furthermore, as illustrated in FIGS. 7A and 7B, even if an angle around the axis of the puncture needle 16 with respect to the puncture site changes, the ultrasonic waves can be reflected toward the probe 42 (FIG. 6) of the ultrasonic imaging device 40 by the reflecting portion 30 including the pair of inclined surfaces 32b and 32b. It is therefore possible to efficiently reflect the ultrasonic waves and obtain a clearer echo image.

As illustrated in FIG. 5, at least one of the pair of inclined surfaces 32b and 32b includes the plurality of inclined flat surfaces 34 having depths from the inner peripheral surface 22s different from each other. The plurality of inclined flat surfaces 34 is included as described above, whereby the ultrasonic waves can be more effectively reflected.

Each of the pair of inclined surfaces 32b and 32b includes the plurality of inclined flat surfaces 34 having depths from the inner peripheral surface 22s different from each other. As a result, even if the angle around the axis of the puncture needle 16 with respect to the puncture site changes, the ultrasonic waves can be reflected by any of the plurality of inclined flat surfaces 34.

Between the plurality of inclined flat surfaces 34, the intermediate flat surface 38 is provided that is parallel to the virtual surface P perpendicular to the axis in the depth direction of the reflecting portion 30. With this configuration, bending angles of corners (edges) are appropriately large that are formed at boundaries between the intermediate flat surface 38 and the inclined flat surfaces 34 respectively adjacent to both sides of the intermediate flat surface 38, so that the ultrasonic waves can be efficiently reflected.

The plurality of inclined flat surfaces 34 may have inclination angles different from each other. With this configuration, there is an increase in the number of angle patterns that can handle the change in the angle around the axis of the puncture needle 16 with respect to the probe 42 (FIG. 6), so that the ultrasonic waves can be more effectively reflected toward the probe 42.

As illustrated by the virtual line in FIG. 5, when the second inclined flat surface 34b has a smaller inclination angle with respect to the virtual surface P perpendicular to the axis a1 in the depth direction of the reflecting portion 30 than that of the first inclined flat surface 34a ($\beta<\alpha$), the ultrasonic waves easily reach the second inclined flat surface 34b, and the ultrasonic waves can be more efficiently reflected.

As illustrated in FIG. 3, the contour shape of the reflecting portion 30 when viewed along the depth direction of the reflecting portion 30 is a quadrangular shape. With this configuration, the ultrasonic waves can be more effectively reflected toward the probe 42.

The reflecting portion 30 is formed in the truncated quadrangular pyramid shape, so that when the reflecting portion 30 is formed by using a metal mold, wear of the distal end portion of the metal mold can be suppressed.

Because the ultrasonic wave reflecting structure 26 includes the plurality of reflecting portions 30, the ultrasonic waves can be more effectively reflected toward the probe 42.

Because the plurality of reflecting portions 30 is arranged in a straight line along the axis a of the puncture needle 16, more reflecting portions 30 can be efficiently arranged.

A puncture needle 56 according to a second embodiment illustrated in FIGS. 8 to 11 is provided with an ultrasonic wave reflecting structure 58 that reflects ultrasonic waves on the needle distal end portion 22. The ultrasonic wave reflecting structure 58 includes at least one reflecting portion 60 having a concave or hole shape that opens on the inner peripheral surface 22s having an arc shape of the needle distal end portion 22. These reflecting portions 60 include openings independent (distinguishable) from each other in the inner peripheral surface 22s of the needle distal end portion 22.

Figure 8:
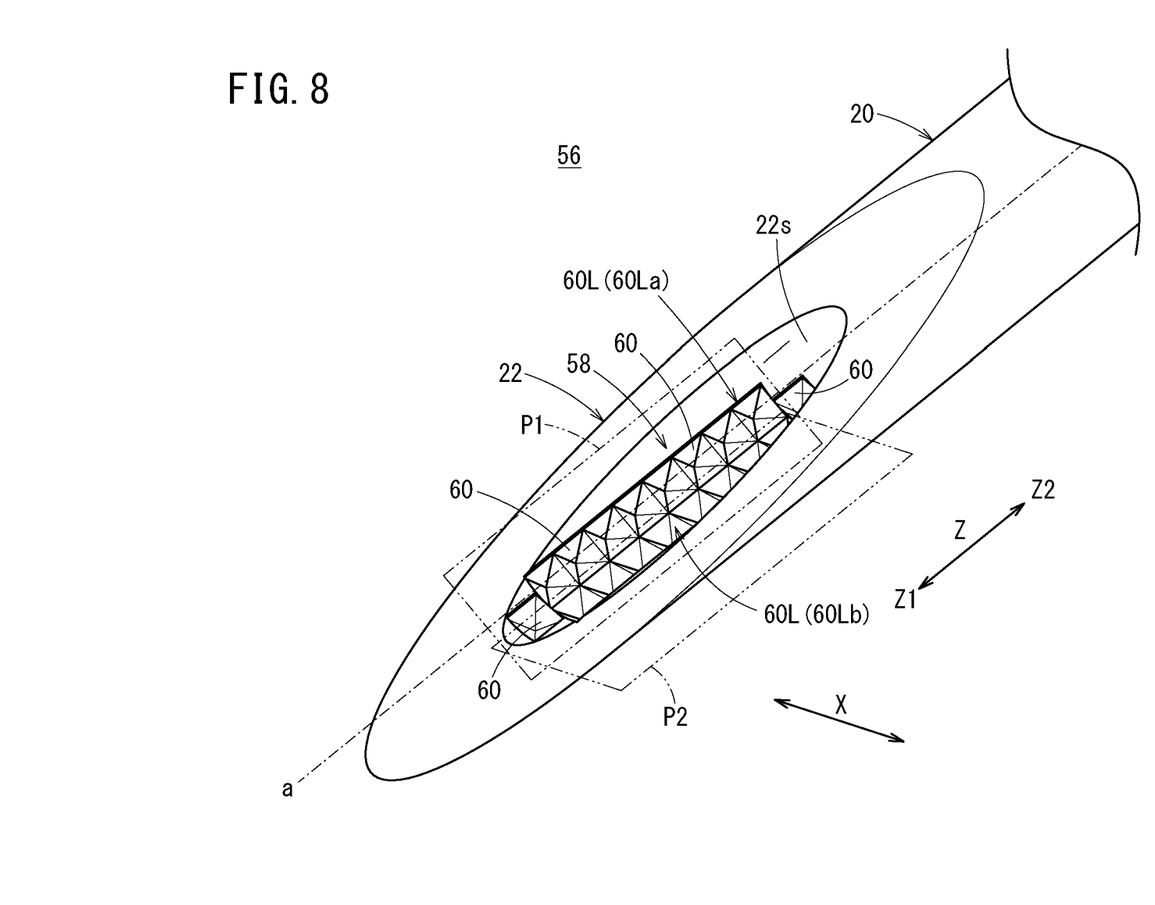
FIG. 8 is a perspective view of a distal portion of a puncture needle according to a second embodiment of the present invention.
Figure 9:
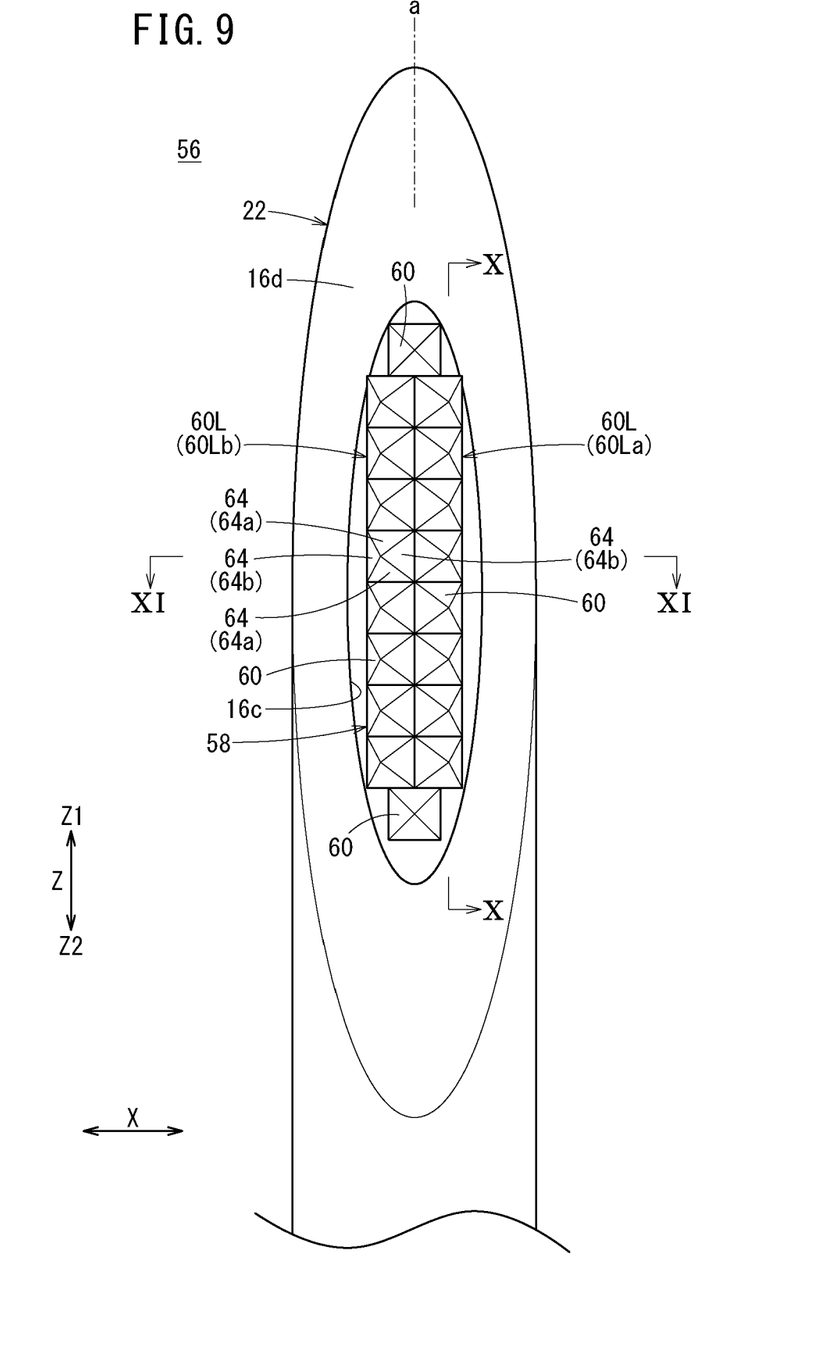
FIG. 9 is a plan view of the distal portion of the puncture needle according to the second embodiment.

In the second embodiment, the ultrasonic wave reflecting structure 58 includes a plurality of the reflecting portions 60. The plurality of reflecting portions 60 is arranged adjacent to each other without any distance from each other. In another aspect, the plurality of reflecting portions 60 may be arranged with a distance from each other. In another aspect, the ultrasonic wave reflecting structure 58 may include only one reflecting portion 60.

As illustrated in FIG. 9, a contour shape of the reflecting portion 60 when viewed along the depth direction of the reflecting portion 60 is a quadrangular shape. The reflecting portion 60 is formed in a quadrangular pyramid shape. In another aspect, the reflecting portion 60 may be formed in a truncated quadrangular pyramid shape. The reflecting portion 60 may be formed in a hole shape penetrating from the inner peripheral surface 22s of the needle distal end portion 22 to the outer peripheral surface.

Figure 11:
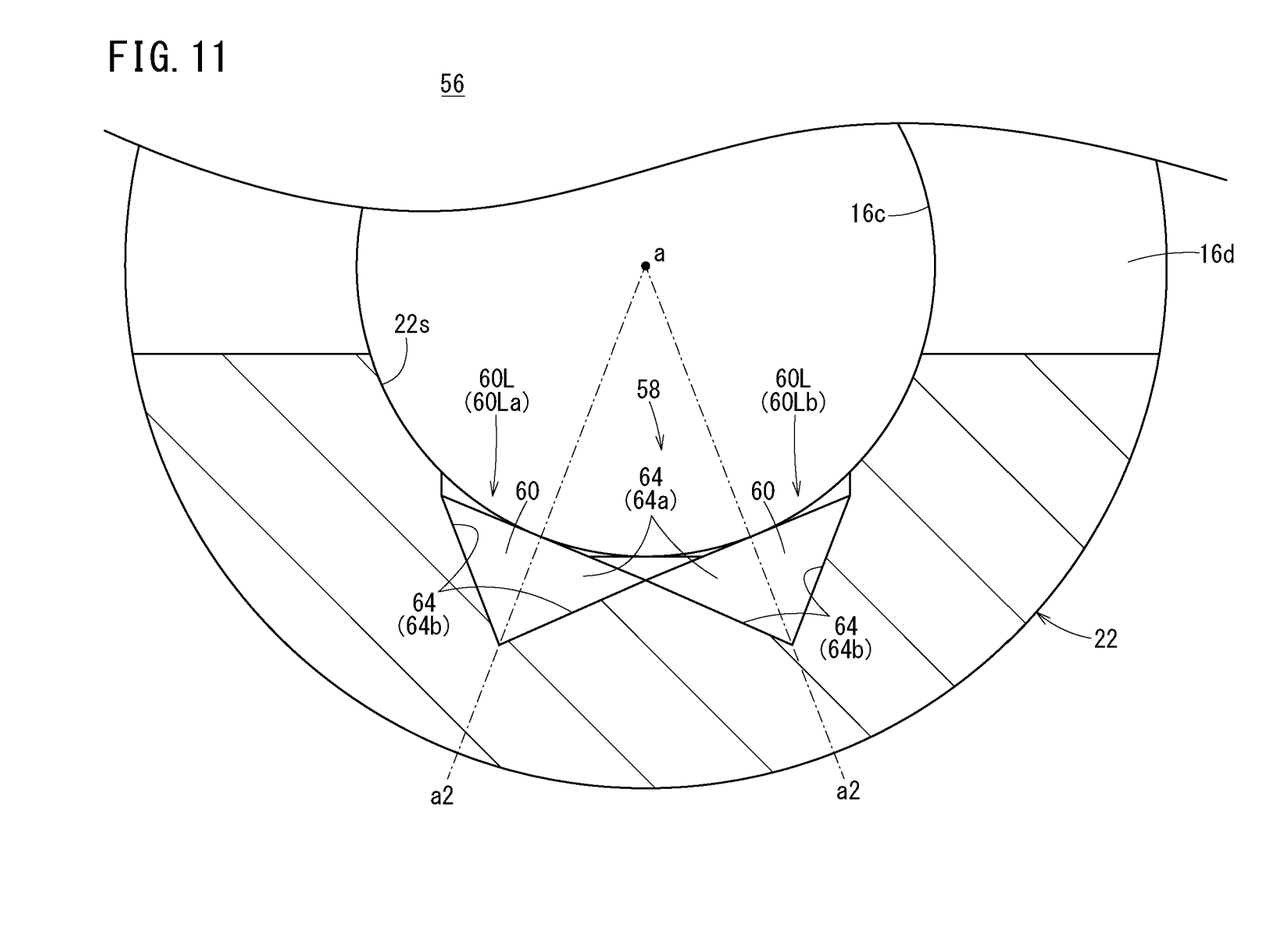
FIG. 11 is a cross-sectional view taken along a line XI-XI of FIG. 9.

The ultrasonic wave reflecting structure 58 includes a plurality of rows 60L (a first row 60La and a second row 60Lb in the illustrated example) each including a plurality of reflecting portions 60 arranged in a straight line. These rows 60L extend parallel to each other. As illustrated in FIG. 11, an axis a2 along the depth direction of the reflecting portion 60 in each row 60L intersects the needle axis a. Thus, between the plurality of rows 60L, the axes a2 along the depth direction of the reflecting portion 60 are inclined to each other.

As illustrated in FIGS. 8 and 9, at the distal end portion of the ultrasonic wave reflecting structure 58, only one reflecting portion 60 is provided at the center in the width direction (arrow X direction) of the distal opening 16c. At the base end portion of the ultrasonic wave reflecting structure 58, only one reflecting portion 60 is provided at the center in the width direction of the distal opening 16c.

Here, as illustrated in FIG. 8, virtual surfaces are defined that are respectively perpendicular to the axes a2 (see FIG. 11) in the depth direction of the reflecting portion 60 (a virtual surface P1 for the first row 60La and a virtual surface P2 for the second row 60Lb). As illustrated in FIG. 9, the inner surface of the reflecting portion 60 includes four inclined surfaces 64 each inclined with respect to the virtual surface. Inclination angles of the four inclined surfaces 64 with respect to the virtual surface are the same as each other. In another aspect, the inclination angles of the four inclined surfaces 64 do not have to be the same as each other.

Figure 10:
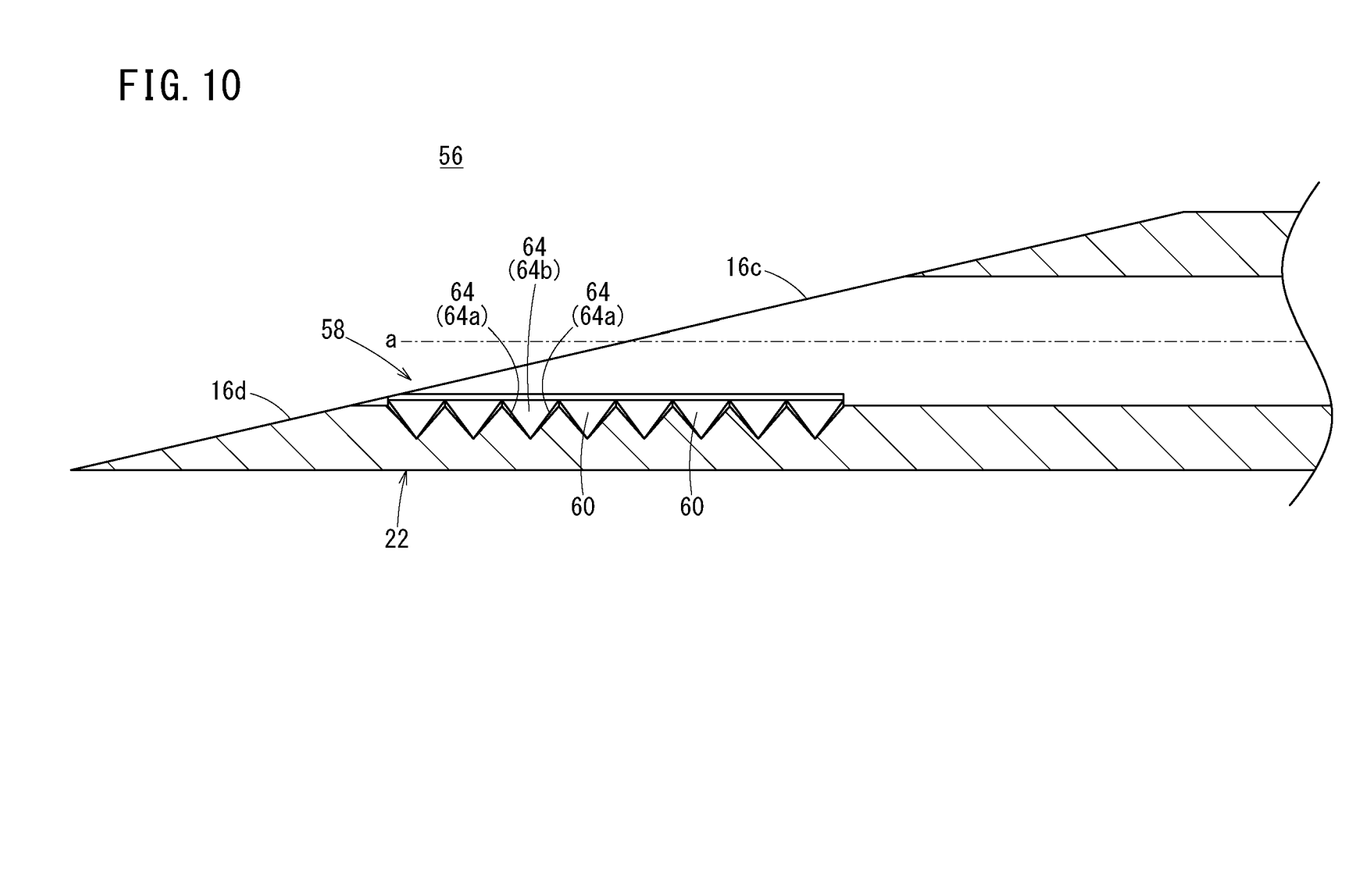
FIG. 10 is a cross-sectional view taken along a line X-X of FIG. 9.

Specifically, the inner surface of the reflecting portion 60 includes a pair of inclined surfaces 64a and 64a facing each other in the needle axis direction (arrow Z direction), and another pair of inclined surfaces 64b and 64b facing each other and each parallel to the needle axis a. As illustrated in FIG. 10, the pair of inclined surfaces 64a and 64a have a distance from each other that becomes smaller as it is closer to the outer peripheral surface side of the needle distal end portion 22. As illustrated in FIG. 11, the pair of inclined surfaces 64b and 64b have a distance from each other that becomes smaller as it is closer to the outer peripheral surface side of the needle distal end portion 22.

Also with the puncture needle 56 according to the second embodiment configured as described above, an effect can be obtained similar to that with the puncture needle 16 according to the first embodiment. That is, because the ultrasonic wave reflecting structure 58 is provided on the inner peripheral surface 22s of the needle distal end portion 22, the position of the needle distal end portion 22 can be easily recognized from the obtained echo image. Furthermore, even if an angle around an axis of the puncture needle 56 with respect to a puncture site changes, the ultrasonic waves can be reflected toward the probe 42 (FIG. 6) of the ultrasonic imaging device 40 by the reflecting portion 60 including the pair of inclined surfaces 64b and 64b. It is therefore possible to efficiently reflect the ultrasonic waves and obtain a clearer echo image.

As illustrated in FIGS. 8 and 9, because the ultrasonic wave reflecting structure 58 includes the plurality of rows 60L each including the plurality of reflecting portions 60 arranged in a straight line, the ultrasonic waves can be more effectively reflected toward the probe 42 (FIG. 6).

In addition, in the second embodiment, for portions common to the first embodiment, the same or similar functions and effects as those of the first embodiment can be obtained.

Note that, the reflecting portion 60 only needs to include at least the pair of inclined surfaces 64b and 64b each parallel to the needle axis a. Thus, in another aspect, the contour shape of the reflecting portion 60 when viewed along the depth direction of the reflecting portion 60 may be a shape other than the quadrangular shape, for example, a hexagonal shape.

The present invention is not limited to the embodiments described above, and various modifications can be made without departing from the gist of the present invention.

What is claimed is:

1. A hollow puncture needle comprising:
a needle body portion;
a needle distal end portion that extends from the needle body portion in a distal direction and that includes a blade surface that is inclined with respect to an axis of the puncture needle; and
an ultrasonic wave reflecting structure comprising a reflecting portion having a concave or hole shape that opens on an inner peripheral surface of the needle distal end portion,
wherein an inner surface of the reflecting portion includes a first inclined surface and a second inclined surface, wherein the first inclined surface faces the second inclined surface, and wherein a distance between the first inclined surface and the second inclined surface becomes smaller in a direction towards an outer peripheral surface side of the needle distal end portion, and
wherein each of the first inclined surface and the second inclined surface is parallel to the axis of the puncture needle and includes a plurality of inclined flat surfaces having depths from the inner peripheral surface different from each other.

2. The puncture needle according to claim 1, wherein:
an intermediate flat surface parallel to a virtual surface perpendicular to an axis in a depth direction of the reflecting portion is provided between the plurality of inclined flat surfaces.

3. The puncture needle according to claim 1, wherein:
the plurality of inclined flat surfaces have inclination angles identical to each other.

4. The puncture needle according to claim 3, wherein:
the plurality of inclined flat surfaces include a first inclined flat surface, and a second inclined flat surface formed at a deeper position from the inner peripheral surface than that of the first inclined flat surface, and
the second inclined flat surface has a smaller inclination angle with respect to a virtual surface perpendicular to an axis in a depth direction of the reflecting portion than that of the first inclined flat surface.

5. The puncture needle according to claim 1, wherein:
the plurality of inclined flat surfaces have inclination angles different from each other.

6. The puncture needle according to claim 1, wherein:
a contour shape of the reflecting portion when viewed along a depth direction of the reflecting portion is a quadrangular shape.

7. The puncture needle according to claim 6, wherein:
the reflecting portion is formed in a truncated quadrangular pyramid shape.

8. The puncture needle according to claim 1, wherein:
the reflecting portion comprises a plurality of reflecting portions.

9. The puncture needle according to claim 8, wherein:
the plurality of reflecting portions are arranged in a straight line along the axis of the puncture needle.

10. The puncture needle according to claim 8, wherein:
the ultrasonic wave reflecting structure comprises a plurality of rows, wherein each row of the plurality of rows comprises some of the plurality of the reflecting portions arranged in a straight line along the axis of the puncture needle.

11. A method of generating an echo image, the method comprising:
providing a hollow puncture needle comprising:
a needle body portion,
a needle distal end portion that extends from the needle body portion in a distal direction and that includes a blade surface that is inclined with respect to an axis of the puncture needle, and
an ultrasonic wave reflecting structure comprising a reflecting portion having a concave or hole shape that opens on an inner peripheral surface of the needle distal end portion,
wherein an inner surface of the reflecting portion includes a first inclined surface and a second inclined surface, wherein the first inclined surface faces the second inclined surface, and wherein a distance between the first inclined surface and the second inclined surface becomes smaller in a direction towards an outer peripheral surface side of the needle distal end portion, and
wherein each of the first inclined surface and the second inclined surface is parallel to the axis of the puncture needle and includes a plurality of inclined flat surfaces having depths from the inner peripheral surface different from each other;
puncturing the needle through skin of a patient toward a blood vessel at a puncture site;
pressing a probe of an ultrasonic imaging device against the skin in a vicinity of the puncture site;
emitting ultrasonic waves from the probe so as to irradiate a distal portion of the needle, and receiving ultrasonic waves that have been reflected by the reflecting structure at the probe; and
generating the echo image based on the reflected ultrasonic waves.

12. The method according to claim 11, wherein:
an intermediate flat surface parallel to a virtual surface perpendicular to an axis in a depth direction of the reflecting portion is provided between the plurality of inclined flat surfaces.

13. The method according to claim 11, wherein:
the plurality of inclined flat surfaces have inclination angles identical to each other.

14. The method according to claim 13, wherein:
the plurality of inclined flat surfaces include a first inclined flat surface, and a second inclined flat surface formed at a deeper position from the inner peripheral surface than that of the first inclined flat surface, and
the second inclined flat surface has a smaller inclination angle with respect to a virtual surface perpendicular to an axis in a depth direction of the reflecting portion than that of the first inclined flat surface.

15. The method according to claim 11, wherein:
the plurality of inclined flat surfaces have inclination angles different from each other.

16. The method according to claim 11, wherein:
a contour shape of the reflecting portion when viewed along a depth direction of the reflecting portion is a quadrangular shape.

17. The method according to claim 16, wherein:
the reflecting portion is formed in a truncated quadrangular pyramid shape.

18. The method according to claim 11, wherein:
the ultrasonic wave reflecting structure comprises a plurality of the reflecting the reflecting portion comprises a plurality of reflecting portions.

19. The method according to claim 18, wherein:
the plurality of reflecting portions are arranged in a straight line along the axis of the puncture needle.

20. The method according to claim 18, wherein
the ultrasonic wave reflecting structure comprises a plurality of rows, wherein each row of the plurality of rows comprises some of the plurality of the reflecting portions arranged in a straight line along the axis of the puncture needle.

21. A hollow puncture needle comprising:
a needle body portion;
a needle distal end portion that extends from the needle body portion in a distal direction and that includes a blade surface that is inclined with respect to an axis of the puncture needle; and
an ultrasonic wave reflecting structure comprising a reflecting portion having a concave or hole shape that opens on an inner peripheral surface of the needle distal end portion,
wherein an inner surface of the reflecting portion includes a first inclined surface and a second inclined surface, wherein the first inclined surface faces the second inclined surface, and wherein a distance between the first inclined surface and the second inclined surface becomes smaller in a direction towards an outer peripheral surface side of the needle distal end portion,
wherein each of the first inclined surface and the second inclined surface is parallel to the axis of the puncture needle,
wherein at least one inclined surface of the first inclined surface and the second inclined surface includes a plurality of inclined flat surfaces having depths from the inner peripheral surface different from each other, and
wherein an intermediate flat surface parallel to a virtual surface perpendicular to an axis in a depth direction of the reflecting portion is provided between the plurality of inclined flat surfaces.

22. A hollow puncture needle comprising:
a needle body portion;
a needle distal end portion that extends from the needle body portion in a distal direction and that includes a blade surface that is inclined with respect to an axis of the puncture needle; and
an ultrasonic wave reflecting structure comprising a reflecting portion having a concave or hole shape that opens on an inner peripheral surface of the needle distal end portion,
wherein an inner surface of the reflecting portion includes a first inclined surface and a second inclined surface, wherein the first inclined surface faces the second inclined surface, and wherein a distance between the first inclined surface and the second inclined surface becomes smaller in a direction towards an outer peripheral surface side of the needle distal end portion,
wherein each of the first inclined surface and the second inclined surface is parallel to the axis of the puncture needle, and
wherein at least one inclined surface of the first inclined surface and the second inclined surface includes a plurality of inclined flat surfaces having depths from the inner peripheral surface different from each other and having inclination angles identical to each other.

23. A hollow puncture needle comprising:
a needle body portion;
a needle distal end portion that extends from the needle body portion in a distal direction and that includes a blade surface that is inclined with respect to an axis of the puncture needle; and
an ultrasonic wave reflecting structure comprising a reflecting portion having a concave or hole shape that opens on an inner peripheral surface of the needle distal end portion,
wherein an inner surface of the reflecting portion includes a first inclined surface and a second inclined surface, wherein the first inclined surface faces the second inclined surface, and wherein a distance between the first inclined surface and the second inclined surface becomes smaller in a direction towards an outer peripheral surface side of the needle distal end portion,
wherein each of the first inclined surface and the second inclined surface is parallel to the axis of the puncture needle,
wherein at least one inclined surface of the first inclined surface and the second inclined surface includes a plurality of inclined flat surfaces having depths from the inner peripheral surface different from each other and having inclination angles identical to each other,
wherein the plurality of inclined flat surfaces include a first inclined flat surface, and a second inclined flat surface formed at a deeper position from the inner peripheral surface than that of the first inclined flat surface, and
wherein the second inclined flat surface has a smaller inclination angle with respect to a virtual surface perpendicular to an axis in a depth direction of the reflecting portion than that of the first inclined flat surface.

* * * * *